United States Patent [19]

Cardenas et al.

[11] 4,296,257
[45] Oct. 20, 1981

[54] PROCESS FOR PRODUCING DIHYDROCARVONE GEOMETRIC ISOMERS

[75] Inventors: Carlos G. Cardenas; Zia U. Din, both of Jacksonville, Fla.

[73] Assignee: SCM Corporation, New York, N.Y.

[21] Appl. No.: 109,989

[22] Filed: Jan. 7, 1980

[51] Int. Cl.$^3$ .................... C07C 45/51; C07C 45/58
[52] U.S. Cl. ................... 568/361; 568/376
[58] Field of Search ............. 568/342, 364, 361, 376, 568/377, 338

[56] References Cited

U.S. PATENT DOCUMENTS 3,538,164  11/1970  Leffingwell .................... 568/376

OTHER PUBLICATIONS

Royals et al., JACS 77, pp. 3405–3408, (1955).
Henbest et al., JCS Part VI, pp. 4596–4604; (1957).
Settine et al., J. Org. Chem., 29, pp. 616–618, (1964).
Royals et al., J. Org. Chem., 31, pp. 1937–1944, (1966).
Settine et al., J. Org. Chem., 32, pp. 2910–2912, (1967).
Rickborn et al., JACS, 90, pp. 4193–4194, (1971).
Rickborn et al., JACS, 93, pp. 1693–1700, (1971).
Russells et al., Science, 172, pp. 1043–1044, (1971).
Kirk, Chem. & Industry, (3), pp. 109–113, (1973).
Chemical Abstracts, vol. 81: 136305h, (1974).

*Primary Examiner*—Natalie Trousof
*Assistant Examiner*—Vera C. Clarke
*Attorney, Agent, or Firm*—Robert A. Sturges; Merton H. Douthitt

[57] ABSTRACT

Cis- and trans-limonene oxides can be separated effectively one from the other by either fractional distillation or by substantially selectively rearranging with acid catalysis at mild temperature said cis-isomer into trans-dihydrocarvone. The distillatively-separated limonene oxide isomers or the remaining unreacted trans-limonene oxide isomer then is available for discrete conversion into a corresponding dihydrocarvone isomer with minimal equilibration by further acid-catalyzed rearranging at mild temperature.

8 Claims, No Drawings

PROCESS FOR PRODUCING DIHYDROCARVONE GEOMETRIC ISOMERS

This invention relates to an improvement in process for the acid-catalyzed rearrangement of liquid phase limonene oxides into dihydrocarvone whereby a substantially pure dihydrocarvone isomer can be produced efficiently.

BACKGROUND OF THE INVENTION

Prior art processing to make dihydrocarvone isomer by this rearrangement delineates the utilization of mixed cis- and trans-limonene oxides to produce a mixture of cis- and trans-dihydrocarvones. A most economic starting material is citrus (d)-limonene to make the starting epoxides. The resulting mixed product, that is cis- and trans-dihydrocarvones, is of value in formulating flavors and perfumes.

The individual dihydrocarvone isomers, that is cis-dihydrocarvone and trans-dihydrocarvone, (if provided selectively say, from citrus limonene) would be of substantially more value, but such dihydrocarvone isomers cannot be separated in practical fashion by fractional distillation. Such cis-isomer is characterized by what often is called a musty and woody odor, the trans-isomer by an odor of spearmint. In admixture one can detract from the other for various organoleptic use. Accordingly, it has been proposed to synthesize the pure dihydrocarvone isomer by other routes which are more expensive, or to separate them by chromatographic processing, also an expensive procedure.

Advantages of the instant invention over prior proposals include the ability to produce reasonably economically a substantially pure cis- or trans-dihydrocarvone isomer based on limonene such as abundant citrus limonene.

The instant invention is based on two surprising discoveries that go counter to general experience in the art of heat treating unsaturated terpenoids in the presence of acid. The first such discovery is that equilibration of a substantially pure dihydrocarvone isomer can be substantially precluded while generating such isomer by the instant acid-catalyzed rearrangement process. The other discovery is that the cis-limonene oxide in a mixture of cis- and trans-limonene oxides can be transformed substantially selectively and discretely into trans-dihydrocarvone. This, of course, means that the remaining trans-limonene oxide can be further processed to make substantially pure cis-dihydrocarvone by implementing the first discovery.

BROAD STATEMENT OF THE INVENTION

The instant invention is an improvement in process for the acid-catalyzed rearrangement of mixed liquid phase cis- and trans-limonene oxides into dihydrocarvone under limonene oxide rearrangement conditions adapted for producing substantially pure cis- and/or trans-dihydrocarvone isomers. The improvement comprises: separating said limonene oxide isomers by either (a) rearranging in the presence of acid catalyst cis-limonene oxide present to trans-dihydrocarvone substantially selectively and terminating this rearrangement before much of the trans-limonene oxide present reacts, or (b) fractionally distilling effectively to separate said limonene oxide isomers, followed by operating said rearrangement individually on at least one of the thus-separated limonene oxide isomers until the corresponding dihydrocarvone isomer is formed to the substantial exclusion of the other; and recovering the dihydrocarvone isomer thus made by aspect (a) or (b) from the resulting reaction mixture.

DETAILED DESCRIPTION OF THE INVENTION

The limonene oxides and dihydrocarvones of interest here can be depicted graphically as follows:

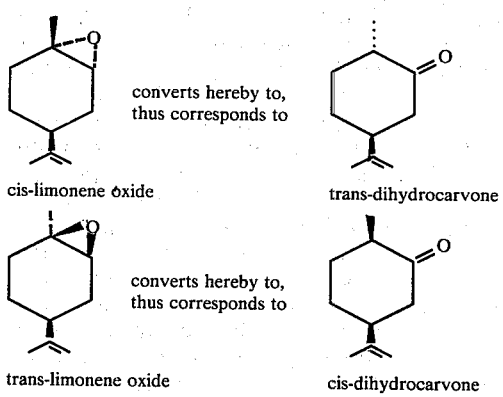

In the art of acid-catalyzed rearrangement of limonene oxides into dihydrocarvones temperatures as low as 0° and as high as 75° C. have been suggested. For most practical selectivity and rapidity in converting a limonene oxide isomer into a dihydrocarvone isomer we find it advantageous, however, to use a temperature between about 50° and about 85° C., and, preferably about 55°–85° C. The temperature can reach even about 95° C. or higher without departing from the precepts of this invention so long as reasonable selectivity is maintained. At a temperature substantially below about 50° C. the reaction appears to be undesirably sluggish, although a high acid strength would be expected to increase the reaction rate. Other acid-catalyzed limonene oxide rearrangement conditions include those of pressure, agitation, concentration and sort of acid catalyst, and dilution with innocuous solvent.

Preferred such pressure is atmospheric for efficiency and economy. Lower and higher pressure can be used, e.g., subatmospheric to 5,000 atmospheres gauge and even higher so long as generally liquid phase conditions prevail. Agitation is desirable, but need not be intensive: Agitation with conventional turbine or propeller apparatus and baffling is adequate. The acid catalyst can be a protic acid or Lewis acid, e.g., sulfuric acid, perchloric acid, lithium perchlorate, and even mixtures of acids. Typically the concentration of acid can be as low as about 0.01% and up to as high as about 10% of the limonene oxide by weight, advantageously is between about 0.1 and about 5% for a Lewis acid, about 0.1 and about 5% for a protic acid, and preferably between about 0.75 and about 1.5% for a Lewis acid and about 0.75 and about 1.5% for a protic acid. Dilution of the reaction is preferred for fluidity and control. In atmospheric pressure rearrangement toluene (or other inert solvent normally boiling near toluene or somewhat higher) in as much as about 5 volumes per volume of limonene oxide is desirable. Frequently a great deal of innocuous solvent, e.g., an ether or a hydrocarbon, can be used with efficiency and economy. The reaction also can be run with (d)-limonene oxide "neat", i.e. simply a fairly pure or technical grade otherwise undiluted.

Fractional distillation of limonene oxides or dihydrocarvones or a mixture of limonene oxide and a dihydrocarvone advantageously is done under relatively low absolute pressure to prevent undesired damage to the feeds or products. Dihydrocarvone is sensitive; it can isomerize readily into carvenone (wherein the isopropenyl "tail" of the dihydrocarvone is turned into an isopropyl "tail" with attendant double bond shifting into the ring alpha to the keto oxygen). Typically distillation conditions are from about 1 to 15 Torr, advantageously 2 to 10 Torr, and distillation generally is operated to keep temperatures from exceeding about 120° C. or even a little lower. The limonene oxides advantageously are fractionally distilled using an efficient distilling apparatus, for example one that includes a spinning band column having performance substantially equivalent to other conventional and efficient fractional distilling apparatus (knowledge of which is fully within the province of the skilled chemist.).

Preparatory to separation and recovery of product and unreacted feedstock, such as by distillation, it is quite desirable to neutralize or otherwise remove acid from the reaction mixture resulting from the rearrangement. Common neutralizing agents such as sodium bicarbonate and the like are useful, and aqueous washing followed by drying the organic phase as over a desiccant (e.g., magnesium sulfate) is respected laboratory practice in this art. Materials of construction for the entire operation are desirably corrosion resistant such as glass, austenitic stainless steel and the like.

The following examples show how this invention has been practiced effectively on a laboratory scale, but are not to be construed as limiting the invention. In this specification all parts are parts by weight, all temperatures are in degrees Celsius, and all parts and percentages are weight parts and percentages unless otherwise expressly noted.

The limonene oxides used in the examples were made by epoxidizing citrus limonene. In the first two examples the cis- and trans-limonene oxide isomers were fractionally distilled under absolute pressure of 10 Torr in a spinning band column to obtain substantially pure cis-limonene oxide and substantially pure trans-limonene oxide for feedstocks.

EXAMPLE 1

A glass reactor equipped with agitator and heater was charged with 1 part lithium perchlorate dissolved in 87 parts of toluene and 20 parts of cis-limonene oxide. Agitation was started and temperature of the reaction mixture maintained at 80°–85° for one hour. At this point the conversion of the limonene oxide was considered substantially complete. The product was worked up by mixing in about 5 parts of water to dissolve lithium salt, whereby some emulsion formed; the product then was further washed with about 20 parts of aqueous sodium chloride solution saturated at room temperature (about 25° C.) to break the emulsion and allow an aqueous layer to separate readily. The aqueous layer was separated from the organic layer. The latter was dried over solid magnesium sulfate particles, then finally fractionally distilled. The ratio of trans-dihydrocarvone to cis-dihydrocarvone in the distillate product was 49:1, a quite pure technical grade of trans-dihydrocarvone.

EXAMPLE 2

The equipment and general procedure used in Example 1 were used also in this example. However, the limonene oxide used was 20 parts of trans-limonene oxide, and the rearrangement temperature was 80° to 85° C. for 4½ hours with a very short interval, a few minutes at most, when the temperature reached 90° to 95° C. At the end of the 4½ hour period conversion of the limonene oxide was considered substantially complete. The ratio of cis-dihydrocarvone to trans-dihydrocarvone in the distillate was 96:4.

EXAMPLE 3

A glass reactor having confirmation and appurtenant equipment quite like that of the isomerization reactor of Example 1 was charged with 2 parts of lithium perchlorate dissolved in 173 parts of toluene and 40 parts of mixed cis- and trans-limonene oxides, such oxide being about 19 parts in the cis configuration. Agitation was vigorous, and the mixture heated at 55° to 60° C. At the end of four hours virtually no cis-dihydrocarvone had formed, but some trans-dihydrocarvone had appeared. The temperature was raised to 80° C. Then, after 30 minutes the ratio of trans- to cis-dihydrocarvone was about 17.1:1.4, and in an hour at 80° C. this ratio had gone to about 31.4 trans-dihydrocarvone to about 3.6 cis-dihydrocarvone. After the reaction was resumed the next day for 30 minutes, the ratio had gone to about 43.6 trans-dihydrocarvone to about 9.7 cis-dihydrocarvone. This ratio represented an essentially complete conversion of the cis-limonene oxide present in the initial charge to trans-dihydrocarvone mixed with only a minor portion of cis-dihydrocarvone.

At this point the reaction was washed and dried as in Example 1. Remaining trans-limonene oxide was separated from the trans-dihydrocarvone product (containing minor cis-dihydrocarvone) by fractional distillation. Such recovered limonene oxide could be reacted in accordance with Example 2 for obtaining additional relatively pure cis-dihydrocarvone. From this work, it became evident that an even purer trans-dihydrocarvone (containing less cis-dihydrocarvone adulterant) could have been obtained by stopping the rearrangement reaction earlier.

In summary, the instant invention can be practiced as follows:
(a) rearranging cis-limonene oxide in a mixture of cis- and trans-limonene oxides substantially selectively to trans-dihydrocarvone;
(b) distillatively separating cis-limonene oxide from trans-limonene oxide in a mixture thereof, then rearranging either or both of the separated oxides substantially selectively into its corresponding dihydrocarvone isomer; or
(c) rearranging part of the cis-limonene oxide as in (a), above, recovering trans-dihydrocarvone as one product, recovering unreacted limonene oxides as a mixture or as materials separate from each other, then proceeding with their rearrangement separately as in (b), above, or rearranging as a mixture to obtain mixed dihydrocarvone isomers.

What is claimed is:
1. A process for producing a single dihydrocarvone isomer from mixed liquid phase cis- and trans-limonene oxide isomers under limonene oxide rearrangement conditions and to the substantial exclusion of the other dihydrocarvone isomer, which comprises:
(A) separating said limonene oxide isomers by either:
(a) rearranging substantially selectively cis-limonene oxide at a temperature of from 50° C. to 95° C. in the presence of an acid catalyst to the trans- dihydrocarvone isomer and terminating this rearrangement before substantial rearrangement of the trans-limonene oxide occurs to form a reaction mixture or (b) first fractionally distilling said limonene oxide isomers to isolate the cis-limonene oxide isomer from the trans-limonene oxide isomer as separate distillate fractions and then rearranging one of the thus-separated limonene isomer distillate fractions in the presence of from 0.1% to 10% by weight of said separated limonene oxide isomer of an acid catalyst, at a temperature of from 50° C. to 95° C., until the corresponding dihydrocarvone isomer is formed in the reaction mixture to the substantial exclusion of the other dihydrocarvone isomer, (B) neutralizing the acid catalyst in said reaction mixture with a base, and (C) recovering the resulting dihydrocarvone isomer from the reaction mixture.

2. The process of claim 1 wherein a distillate fraction consisting essentially of cis-limonene oxide is rearranged to make trans-dihydrocarvone.

3. The process of claim 1 wherein a distillate fraction consisting essentially of trans-limonene oxide is rearranged to make cis-dihydrocarvone.

4. The process of claim 1 wherein trans-limonene oxide, remaining in the reaction mixture from which said trans-dihydrocarvone product according to step (A)-(a) was recovered, is rearranged substantially selectively in the presence of from 0.1% to 10% by weight of the trans-limonene oxide of an acid catalyst at a temperature of from 55° C. to 95° C. to convert it into cis-dihydrocarvone, and the cis-dihydrocarvone thus formed then is recovered.

5. The process of claim 1 wherein the catalyzing acid is a Lewis acid.

6. The process of claim 5 wherein said Lewis acid is lithium perchlorate.

7. The process of claim 6 wherein the rearrangement temperature is between about 55° and about 85° C.

8. The process of claim 1 wherein said separating of the limonene oxide isomers is done by first rearranging part of said cis-limonene oxide into trans-dihydrocarvone product with very little rearrangement of the trans-limonene oxide present into cis-dihydrocarvone, and said product and remaining unreacted limonene oxide isomers each are recovered, the recovered remaining limonene oxide isomers being separate from said product as either a blend containing cis- and trans-limonene oxides or as substantially distinct cis- and trans-limonene oxide-containing portions.

* * * * *